US00PP33772P2

(12) United States Plant Patent
Williams

(10) Patent No.: US PP33,772 P2
(45) Date of Patent: Dec. 21, 2021

(54) ***COLOCASIA* PLANT NAMED 'PHARAOHS MASK'**

(50) Latin Name: ***Colocasia* hybrid**
Varietal Denomination: Pharaohs Mask

(71) Applicant: Brian Paul Williams, Louisville, KY (US)

(72) Inventor: Brian Paul Williams, Louisville, KY (US)

(73) Assignee: BRIAN'S BOTANICALS, Louisville, KY (US)

( * ) Notice: Subject to any disclaimer, the term of this patent is extended or adjusted under 35 U.S.C. 154(b) by 0 days.

(21) Appl. No.: 17/103,955

(22) Filed: Nov. 25, 2020

(51) Int. Cl.
*A01H 5/12* (2018.01)
*A01H 6/10* (2018.01)

(52) U.S. Cl.
USPC ..... Plt./373

(58) Field of Classification Search
USPC ..... Plt./373
See application file for complete search history.

(56) References Cited

U.S. PATENT DOCUMENTS

PP29,870 P2 * 11/2018 Garner ..... A01H 5/02
Plt./373

* cited by examiner

*Primary Examiner* — Susan McCormick Ewoldt
*Assistant Examiner* — Karen M Redden
(74) *Attorney, Agent, or Firm* — Penny J. Aguirre

(57) ABSTRACT

A new cultivar of *Colocasia* plant named 'Pharaohs Mask' that is characterized by its clump forming growth habit, its plant height up to 1.5 m, its leaves that are green in color with margins that are curled under, its leaves that are green in color with margins that are curled under, its petioles that are dark black in color, and its leaf veins that are dark black in color, prominent, and raised starting at the mid-vein and running to the edge of the leaves.

2 Drawing Sheets

Botanical classification: *Colocasia* hybrid.
Cultivar designation: 'Pharaohs Mask'.

BACKGROUND OF THE INVENTION

The present invention, *Colocasia* 'Pharaohs Mask', relates to a new and distinct of *Colocasia* plant of hybrid origin and is hereinafter referred to by its cultivar name, 'Pharaohs Mask'. 'Pharaohs Mask' is a new tropical plant used as a landscape and container plant in tropical and subtropical areas.

The new cultivar was derived from a controlled breeding program conducted by the Inventor at his nursery in Louisville, Ky. The overall purpose of the breeding program is to make selections of *Colocasia* plants with colorful foliage with distinctive leaf veins. 'Pharaohs Mask' arose from a cross made in June of 2013 between *Colocasia* 'Dark Star' (not patented) as the female parent and an unpatented and unnamed proprietary plant of *Colocasia fontanesii* from the Inventor's breeding program as the male parent. 'Pharaohs Mask' was selected as a single unique plant in August of 2018 from amongst the seedlings derived from the above cross.

Asexual propagation of the new cultivar was first accomplished by root cuttings by the Inventor in Louisville, Ky. in August of 2018. Asexual propagation by root cuttings and tissue culture using meristematic tissue has shown that the characteristics of the new cultivar are stable and reproduced true to type in successive generations.

SUMMARY OF THE INVENTION

The following traits have been repeatedly observed and represent the characteristics of the new cultivar. These attributes in combination distinguish 'Pharaohs Mask' as a new and unique cultivar of *Colocasia*.

1. 'Pharaohs Mask' exhibits a clump forming growth habit.
2. 'Pharaohs Mask' exhibits a plant height up to 1.5 m.
3. 'Pharaohs Mask' exhibits leaves that are green in color with margins that are curled under.
4. 'Pharaohs Mask' exhibits petioles that are dark black in color.
5. 'Pharaohs Mask' exhibits leaf veins that are dark black in color, prominent, and raised starting at the mid-vein and running to the edge of the leaves.

The female parent of 'Pharaohs Mask' differs from 'Pharaohs Mask' in having a "v" shaped pattern on the leaf, flat leaf edges, and petioles that are green in color. The male parent of 'Pharaohs Mask' differs from 'Pharaohs Mask' in having leaves that are dark green in color without distinct veins and a taller plant height, and in lacking a clump-forming growth habit with runners produced. 'Pharaohs Mask' can be most closely compared to the *Colocasia* cultivars 'Black Sapphire Gecko' (U.S. Plant Pat. No. 27,966) and 'Nancy's Revenge' (not patented). 'Black Sapphire Gecko' is similar to 'Pharaohs Mask' in having heart shaped leaves and dark black petioles. 'Black Sapphire Gecko' differs from 'Pharaohs Mask' in having leaves that are dark purple-black in color on the upper surface and maroon in color on the lower surface that lack prominent veins and curled margins. 'Nancy's Revenge' is similar to 'Pharaohs Mask' in having large, heart shaped leaves and a clumping growth habit. 'Nancy's Revenge' differs from 'Pharaohs Mask' in having leaves that are light green in color with creamy white centers that lack curled margins and petioles that are green in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but may not be limited to website listings by Brian's Botanical (the Inventor's company), Plants Nouveau (the Inventor's representative for licensing), Little Prince Plants, Eldon Tropicals, the Plant Whore, ebay, McNaughton's Garden Center, AG3, and Blue Moon Tropicals.

BRIEF DESCRIPTION OF THE DRAWINGS

The accompanying colored photographs illustrate the overall appearance and distinct characteristics of the new *Colocasia*, 'Pharaohs Mask'. The photographs were taken of an eight-month-old plant as grown outdoors in a trial garden in Louisville, Ky.

The photograph in FIG. 1 provides an overall view of the mature foliage and plant habit of 'Pharaohs Mask'.

Figure 1:
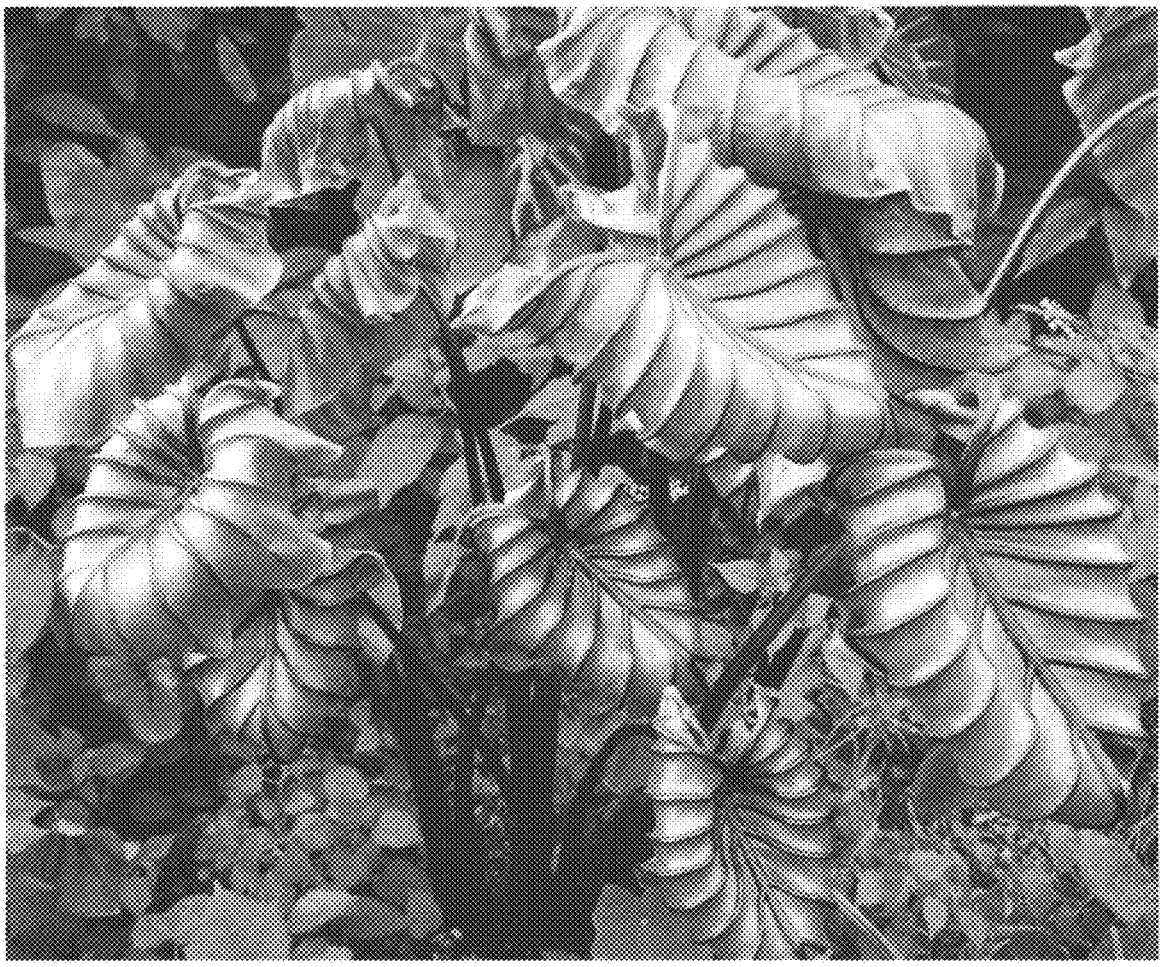
Figure 2:
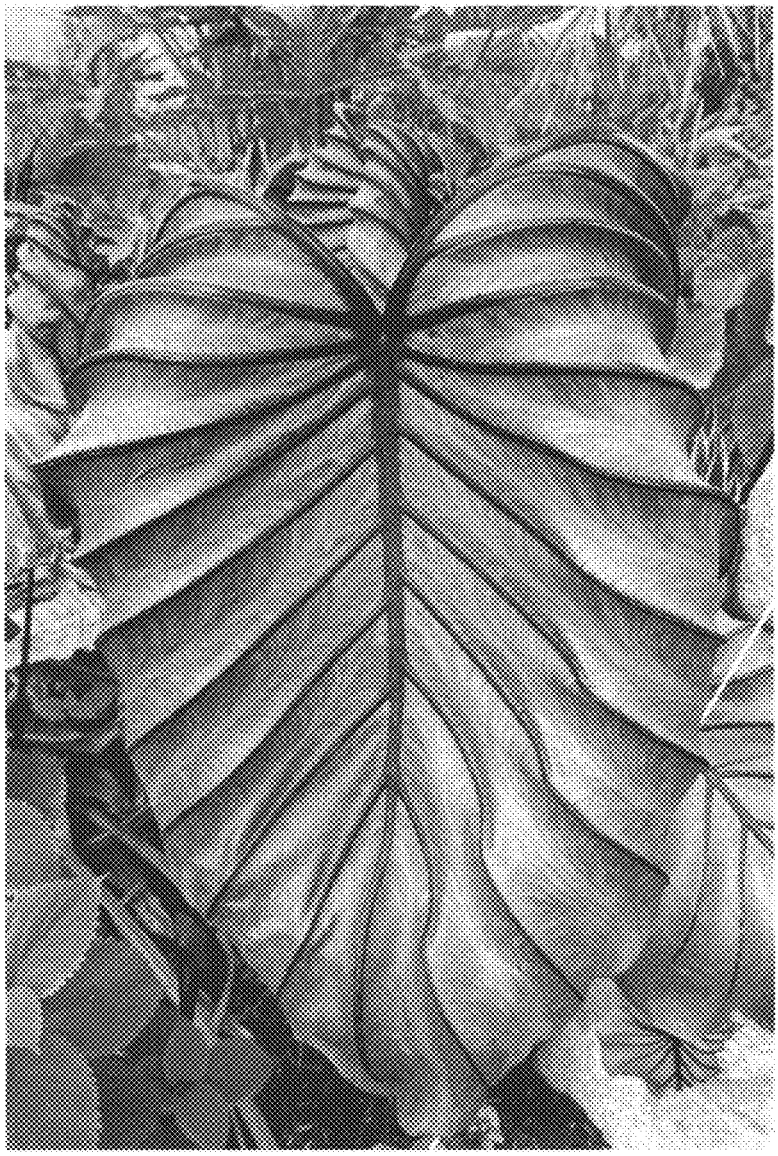

The photograph in FIG. 2 provides a close-up view of the upper surface of a leaf of 'Pharaohs Mask'.

The colors in the photographs are as close as possible with the digital photography techniques available, the color values cited in the detailed botanical description accurately describe the colors of the new *Colocasia*.

DETAILED BOTANICAL DESCRIPTION OF THE PLANT

The following is a detailed description of 2-month plants from a tissue culture plug in a 2-quart container with mature data taken from one or two-year-plants of the new cultivar as grown in one-gallon containers outdoors under two mm poly in Louisville, Ky. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—Periodically around the year depending on temperatures in Kentucky.

*Plant type.*—Tropical perennial herb.

*Plant habit.*—Upright, stemless, clump forming.

*Height and spread.*—30 cm in height, 15 cm in width as a one-year-old plant in a container, mature plant reaches up to 1.5 m in height and 1.2 m in width.

*Hardiness.*—At least in U.S.D.A. Zones 7 to 10.

*Diseases and pests.*—No resistance or susceptibility to diseases and pests has been observed.

*Roots.*—Fleshy, NN155D in color.

*Propagation type.*—Root cuttings and tissue culture.

*Growth rate.*—Vigorous.

*Root development.*—Root initiate in 3 to 5 weeks and a young plant is produced in 3 to 6 weeks from a rooted cutting.

*Stem description.*—Stemless, can produce large tubers with age; formed at the base of the petioles with age, about 16 to 20 cm in diameter and 9 cm in height on a 2-year-old plant, comprised of petiole scales, surface is rough and paper-like, color is a blend of N199B and N199C, main tubers are circular in shape with side tubers cylindrical in shape.

Foliage description:

*Leaf shape.*—Cordate.

*Leaf division.*—Single.

*Leaf base.*—Cordate.

*Leaf apex.*—Acute.

*Leaf venation.*—Pinnate, upper surface; raised, prominent, N200A in color with veins extending to margin edges, lower surface not prominent and matches leaf color.

*Leaf margins.*—Entire, slightly undulate, and strongly curled under.

*Leaf attachment.*—Petiolate.

*Leaf arrangement.*—Single.

*Leaf surface.*—Upper and lower surface; glossy to slightly glossy, rugose, coriaceous, and glabrous.

*Leaf orientation.*—Held downward.

*Leaf color.*—Both surfaces a blend of 144A and 137C.

*Leaf size.*—Average of 16 cm in length and 9 cm in width.

*Leaf sinus depth.*—Average of 3.5 cm.

*Petioles.*—Held erect to semi-erect, an average of 29 cm in length and 1 cm in diameter, glaucescent surface, N200A in color, the basal sheath portion is triangular in shape, top portion round in shape.

Inflorescence description:

*Inflorescence type.*—Spadix surrounded by a spathe, male portion held above female portion, only female flowers are developed.

*Inflorescence size.*—An average of 26 cm in length and 2 cm in width.

*Inflorescence bud.*—Linear to slightly narrow lanceolate in shape, an average of 14 cm in length and 3 cm in width.

*Flower fragrance.*—None.

*Lastingness of inflorescence.*—Inflorescence blooms intermittently during the bloom period, individual flowers last about 2 to 3 weeks.

*Inflorescence/flower quantity.*—An average of 150 female flowers sessile to spadix, sessile male flowers are undeveloped.

*Spathe.*—Hooded, bract, subtending spadix, an average of 21 cm in length and 1.5 cm in width, entire margin, bottom portion; elliptic and balloon shaped, an average of 4.5 cm in length and 2 cm in width, apex fused to upper portion, truncate base, upper portion (hood); round in shape, an average of 17 cm in length and 1.3 cm in width, acute apex, upper and lower portion inner and outer surface; coriaceous and smooth, color: upper portion outer surface; 151A to 151B, upper portion inner surface; 2C, lower portion outer surface; a blend of 144B and N92A, lower portion inner surface; 144A.

*Spadix.*—Male portion above female zone, upright linear in shape (phallus like), apex narrowly pointed, an average of 5.5 cm in length and 6 mm in width, a mix of N187A to N187B and N155C towards the base in color, female portion; ovate in shape, an average of 4.7 cm in length and 1 cm in width, a mix of N155C and 144A in color.

*Peduncle.*—Grows from base of plant, triangular in shape, an average of 9 cm in length and 8 mm in diameter, durable and strong, a blend of N92A and 187A, coriaceous, glabrous, and smooth surface.

Reproductive organs:

*Gynoecium.*—1 minute pistil with an average of 5 carpels, base 144A, top 150C in color, ovary is round in shape, full of many small ovules, 2 mm in length and N155C in color.

*Androecium.*—Undeveloped.

*Fruit and seed.*—None produced.

It is claimed:

1. A new and distinct cultivar of *Colocasia* plant named 'Pharaohs Mask' as herein illustrated and described.

* * * * *